:::

United States Patent [19]
Vlasov et al.

[11] Patent Number: 5,464,511
[45] Date of Patent: Nov. 7, 1995

[54] CHALCOGENIDE ION SELECTIVE ELECTRODES

[76] Inventors: Yuri G. Vlasov, Budapestskaja ul 98, k 1, kv305, St. Petersburg 192281, Russian Federation; Yeugeni A. Bychkov, Max-Planck-Str. 7, 76344 Leopoldshaten, Germany

[21] Appl. No.: 298,765

[22] Filed: Aug. 31, 1994

Related U.S. Application Data

[62] Division of Ser. No. 157,950, Nov. 24, 1993, Pat. No. 5,366,936.

[51] Int. Cl.⁶ ............................................. G01N 27/26
[52] U.S. Cl. ................... 204/153.1; 204/416; 204/419; 204/153.13
[58] Field of Search .................... 204/416, 419, 204/153.1, 153.13

[56] References Cited

U.S. PATENT DOCUMENTS

| | | | |
|---|---|---|---|
| 3,591,646 | 7/1971 | Frant et al. | 204/419 |
| 3,709,813 | 1/1973 | Johnson et al. | 204/419 |
| 4,413,343 | 11/1983 | Fakuda et al. | 372/44 |
| 5,032,358 | 7/1991 | Helenius | 420/500 |

OTHER PUBLICATIONS

New solid–state ion–selective electrodes—Sensors for chemical analysis of solutions, Y. G. Vlasov, Fresenius Z Anal CHem (1989) 335:92–99.

Edirotial—Twenty Years of Ion–Selective Electrodes, Ion–Selective Electrode Rev., Yu. G. Vlasov and E. A. Bychkov, 1987, vol. 9, pp. 1–3.

Ion Selectie Electrochemical Sensors—$Fe^{+3}$, $CU^{+2}$, Charles T. Baker and Isaac Trachtenberg, J. Electrochem. Soc.: Electrochemical Science, vol. 118, No. 4, pp. 571–576.

Lead Ion–Selective Electrodes, Yu. G. Vlasov and E. A. Bychkov, Chalcogenide Glass Electrodes, pp. 6–93.

*Primary Examiner*—John Niebling
*Assistant Examiner*—Bruce F. Bell
*Attorney, Agent, or Firm*—Kokjer, Kircher, Bowman & Johnson

[57] ABSTRACT

A novel series of chalcogenide glass compositions that are relatively highly selective for a specific ion in solution. When utilized as a sensing element for electrodes or similar analytical devices, a modified surface layer is formed on the surface of the glass in contact with the test solution. The surface layer being characterized by a surface ionic conductivity ranging from $10^{-7}$ to $10^{-2}$ S/cm, a diffusion coefficient ranging from $10^{-11}$ to $10^{-6}$ cm$^2$/s and having a ratio of electronic to ionic conductivity within the modified surface layer of not more than 1.0. Specific compositions having these unique morphology and transport properties are disclosed for the detection of cadmium, silver, thallium, mercury, copper and lead.

8 Claims, No Drawings

CHALCOGENIDE ION SELECTIVE ELECTRODES

This is a division of application Ser. No. 08/157,950, filed Nov. 24, 1993, now U.S. Pat. No. 5,366,936.

BACKGROUND OF THE INVENTION

1. Field of the Invention

The present invention relates generally to the field of electrochemical detection, and is more particularly directed to a series of novel chalcogenide glass compositions that may be used as sensor materials for the selective detection of metallic ions in solution.

2. Description of the Related Art

With the advent of ion selective electrodes (also known as ISEs), the use of electrochemical detection in industrial and medical applications has virtually exploded over the last few decades. ISEs provide a viable and convenient means for measuring the concentration of a specific ionic species in solution. In so doing, flowing samples can be continuously monitored such as to insure water quality, to identify contaminant levels in industrial effluent, and to attain optimum yields in chemical processes. Aside from the more conventional ISEs having an internal reference solution and electrode, solid state devices such as all solid state ISEs which are somewhat more durable are being developed. In addition, ion selective field effect transistors (ISFETs) are known which are so compact as to potentially enable implantation in patients, for example, to monitor critical ionic levels during surgery and the like.

The sensor materials utilized in ISEs and ISFETs to construct the sensing element or selective membrane of the device, generally need exhibit ionic conductivity and be selective or responsive to a specific ionic species. Known sensor materials include crystalline electrolytes such as pressed pellets of silver sulfide by itself or in combination with silver halides or other sulfide salts. See e.g. U.S. Pat. No. 3,591,464 to Frant. While these crystalline materials have utility, their overall performance in terms of selectivity can be altered in the presence of corrosive media such as acids and in the presence of strong oxidizing agents. In addition, the crystalline structure may be less durable in certain environments so as to detract from potential stability at the crystalline membrane surface over time. For these reasons, particularly in the case of solid state ISEs and ISFETs, there is a need to improve sensor materials known in the art to provide a stable device in varying environments and over long periods of usage.

Another type of sensor material known in the field is chalcogenide glass. Chalcogens, the elements of the sixth group of the Periodic Table including sulfur, selenium and tellurium as well as their binary, ternary and multi-component compounds with the elements of the third, fourth and firth groups such as germanium, phosphorous and antimony, can be readily obtained as amorphous vitreous solids. Chalcogenide glasses are promising membrane materials, particularly for solid-state ISEs and ISFETs, because they are generally more chemically stable in comparison with the corresponding crystalline materials.

Chalcogenide glass membranes comprising 60% selenium (Se), 28% germanium (Ge) and 12% antimony (Sb), and doped with elemental iron, cobalt and/or nickel were early on developed showing a selective response to iron ($Fe^{+3}$) and copper ($Cu^{+2}$) ions. C. T. Baker and I. Trachtenberg, J. Electrochem. Soc., 118. 329 (1971). Other vitreous chalcogenide compositions have since been disclosed which exhibit sensitivity to other metallic ions in solution including copper, lead, cadmium and silver for example. See, Yu. G. Vlasov and E. A. Bychkov, Ion-Selective Electrode Rev., 1987, Vol. 9, pp. 5–89 (made a part hereof and incorporated herein by reference). These chalcogenide membranes showed little change in selectivity even in the presence of strong acids and oxidation agents. Furthermore, the electric properties of these amorphous solids appear uneffected by occasional impurities which could otherwise negatively impact consistency of results.

In conjunction with their investigations respecting chalcogenide electrode materials, the present inventors observed that certain chalcogenide glass membranes develop a modified surface layer on the membrane surface upon contact with a test ionic solution. This modified layer is characterized by a considerable concentration of exchange sites for ion migration from the solution to the exchange sites and vice versa. It is believed that the direct ion exchange between solution and this modified surface layer is a potential-generating process that is extremely stable. Thus, the inventors next area of inquiry resided in developing specific chalcogenide formulations that would include this modified surface having a high concentration of ionic exchange sites, and further have the ability to affect a gradual transition from ionic conductivity at the membrane/solution interface to electronic conductivity for measurement. Excessive electronic conductivity would detract from the selectivity of the electrode, while too low a value of electronic conductivity would hinder its use in all solid state and ISFET devices. In combination with those attributes, the inventors sought specific chalcogenide compositions that exhibited high selectivity for specific ions in solution, even higher than conventional crystalline materials, so as to provide not only a more durable and stable electrochemical device but to provide a more sensitive device as well.

Thus, it is a primary object of the present invention to provide a chalcogenide glass sensor material for measuring the presence of ions in solution that is relatively highly selective for a specific ion in solution.

It is another object of the present invention to provide an improved chalcogenide glass sensor material that is durable and effective over extended periods of in-use service.

A further object of the present invention is to provide a chalcogenide glass sensor material that exhibits relatively high precision, stability and reproducibility of measurement.

It is also an object of the present invention to provide a chalcogenide glass sensor material that is relatively stable in the presence of oxidizing agents and corrosive media such as strongly acidic media.

Another object of the present invention is to provide a chalcogenide glass sensor material that exhibits both ionic conductivity and electronic conductivity in such a manner as to affect a gradual transition of ionic conductivity to electronic conductivity for measurement.

Yet another object of the present invention is to provide a chalcogenide glass sensor material that is particularly suitable for use in an all solid state ISEs and ISFETs constructed to achieve all the objects heretofore set forth.

A further object of the present invention is to provide a novel chalcogenide glass sensor material for the selective detection of cadmium.

Another object of the present invention is to provide a novel chalcogenide glass sensor material for the selective detection of copper.

Yet a another object of the present invention is to provide a novel chalcogenide glass sensor material for the selective detection of silver.

Still a further object of the present invention is to provide a novel chalcogenide glass sensor material for the selective detection of lead.

It is another object of the present invention to provide a novel chalcogenide glass sensor material for the selective detecting of thallium.

It is yet a further object of the present invention to provide a novel chalcogenide glass sensor material for the selective detection of mercury.

Still another object of the present invention is to provide an electrochemical device for the selective detection of metallic ions in solution comprising a novel chalcogenide glass sensor material as heretofore described.

SUMMARY OF THE INVENTION

These and other objects are achieved by a novel series of chalcogenide glass compositions that are relatively highly selective for a specific ion in solution. The glass compositions made in accordance with this invention are characterized by a unique morphology, wherein a modified surface layer forms on the surface of the glass upon initial contact with an aqueous test solution. This modified surface layer has a thickness generally ranging from about 20 nanometer (nm) to 200 nm and exhibits a surface ionic conductivity ranging from $10^{-7}$ to $10^{-2}$ S/cm and a diffusion coefficient ranging from $10^{-11}$ to $10^{-6}$ cm$^2$/s. It is believed that the specific morphology and transport properties of this modified surface layer of the chalcogenide glass provides a material having high ionic exchange current density at the glass membrane/solution interface resulting in enhanced sensor properties.

The ratio of electronic to ionic conductivity within the modified surface layer is preferably not more than 1.0, which affects a stable and reproducible transition from ionic conductivity at the modified membrane layer to electronic conductivity for measurement. Although the inventors do not wish to be limited by theory, it is hypothesized that glasses with higher ionic conductivity in the modified surface layer display less chemical stability and potential reproducibility, while glasses with lower surface ionic conductivity and comparable electronic conductivity reveal less sensitivity and selectivity to primary ions.

Specific compositions having these unique morphology and transport properties have been developed for the detection of cadmium, silver, thallium, mercury, copper and lead. These materials perform well and are highly selective and stable even in the presence of acidic solutions and strong oxidizing agents.

DETAILED DESCRIPTION OF THE INVENTION

A series of chalcogenide glass sensor materials in accordance with this invention may be used to construct electrode membranes for the selective detection of a specific ion in solution. The glass materials are characterized by a unique surface morphology wherein a modified surface layer is formed on the membrane when contacted with an aqueous solution. The modified surface layer has a thickness ranging from about 20 to 200 nm, a surface ionic conductivity ranging from $10^{-7}$ to $10^{-2}$ S/cm, and a diffusion coefficient ranging from $10^{-11}$ to $10^{-6}$ cm$^2$/s. The ratio of electronic to ionic conductivity within the surface layer is preferably not more than 1.0.

In one embodiment of the present invention, a chalcogenide glass sensor material is provided for the selective detection of cadmium, and comprises cadmium (Cd), silver (Ag), arsenic (As), iodide (I), antimony (Sb) and sulfur (S) in the amount ranges based on gram-atomic weight percents as follows:

| Element | Gram-Atomic Weight % of Total |
| --- | --- |
| Cd | 1–7 |
| Ag | 8–30 |
| As | 15–30 |
| Sb | 2–10 |
| I | 6–18 |
| S | remainder |

Examples of suitable chalcogenide glass compositions in accordance with this invention for the selective detection of cadmium include $Cd_1Ag_{30}As_{24}Sb_2I_6S_{37}$, $Cd_2Ag_8As_{30}Sb_5I_{10}S_{45}$, $Cd_2Ag_{17}As_{23}Sb_3I_{12}S_{43}$, $Cd_4Ag_{22}As_{16}Sb_5I_{14}S_{39}$, and $Cd_7Ag_{15}As_{15}Sb_{10}I_{18}S_{35}$, with $Cd_2Ag_{17}As_{23}Sb_3I_{12}S_{43}$ most preferred for purposes of the present invention.

A chalcogenide glass sensor for the detection of lead in accordance with the present invention comprises lead (Pb), silver (Ag), germanium (Ge), iodide (I) and sulfur (S) in the amounts as follows:

| Elements | Gram-atomic Weight % of Total |
| --- | --- |
| Pb | 3–15 |
| Ag | 10–30 |
| Ge | 10–25 |
| I | 5–20 |
| S | remainder |

Examples of suitable lead selective compositions include $Pb_3Ag_{30}Ge_{18}I_5S_{44}$, $Pb_4Ag_{10}Ge_{25}I_{12}S_{49}$, $Pb_{10}Ag_{22}Ge_{10}I_{14}S_{44}$, $Pb_{13}Ag_{19}Ge_{13}I_{15}S_{40}$, and $Pb_{15}Ag_{14}Ge_{15}I_{20}S_{36}$, with $Pb_{13}Ag_{19}Ge_{13}I_{15}S_{40}$ being most preferred.

A chalcogenide glass sensor for the detection of silver comprising silver (Ag), germanium (Ge) and selenium (Se) may be provided as follows:

| Elements | Gram-atomic Weight % of Total |
| --- | --- |
| Ag | 6–30 |
| Ge | 25–40 |
| Se | remainder |

Examples of silver selective compositions in accordance with this invention include $Ag_6Ge_{40}Se_{54}$, $Ag_{15}Ge_{35}Se_{50}$, $Ag_{19}Ge_{30}Se_{51}$ and $Ag_{30}Ge_{25}Se_{45}$, with $Ag_{15}Ge_{35}Se_{50}$ being most preferred.

A chalcogenide glass sensor for the detection of thallium ions in accordance with the present invention comprises thallium (Tl), germanium (Ge) and selenium (Se) in the amount ranges as follows:

| Elements | Gram-atomic Weight % of Total |
| --- | --- |
| Tl | 20–35 |
| Ge | 14–40 |
| Se | remainder |

Examples of suitable thallium selective compositions include $Tl_{20}Ge_{40}Se_{40}$, $Tl_{24}Ge_{30}Se_{46}$, $Tl_{28}Ge_{14}Se_{58}$ and $Tl_{35}Ge_{16}Se_{49}$ with $Tl_{28}Ge_{14}Se_{58}$ being preferred.

A chalcogenide glass sensor for the selective detection of copper ions may be provided in accordance with the present invention comprising copper (Cu), silver (Ag), germanium (Ge) and selenium (Se) in the amount ranges as follows:

| Elements | Gram-atomic weight % of Total |
|---|---|
| Cu | 5–20 |
| Ag | 5–20 |
| Ge | 18–32 |
| Se | remainder |

Examples of suitable copper selective compositions include $Cu_5Ag_{20}Ge_{30}Se_{45}$, $Cu_{10}Ag_{10}Ge_{32}Se_{48}$, $Cu_{15}Ag_{12}Ge_{22}Se_{51}$, and $Cu_{20}Ag_5Ge_{18}Se_{57}$, with $Cu_{10}Ag_{10}Ge_{32}Se_{48}$ being most preferred.

A chalcogenide glass sensor for the selective detection of mercury may be provided comprising mercury (Hg), silver (Ag), iodide (I), arsenic (As), antimony (Sb) and sulfur in the amount ranges as follows:

| Elements | Gram-atomic Weight % of Total |
|---|---|
| Hg | 2–10 |
| Ag | 25–40 |
| As | 7–16 |
| I | 2–30 |
| Sb | 1–5 |
| S | remainder |

Examples include $Hg_2Ag_{25}As_{16}Sb_4I_{23}S_{30}$, $Hg_4Ag_{35}As_{10}Sb_1I_{25}S_{25}$, $Hg_4Ag_{40}As_8Sb_3I_{23}S_{22}$, $Hg_7Ag_{34}As_7Sb_5I_{30}S_{17}$, and $Hg_{10}Ag_{26}As_{12}Sb_4I_{20}S_{28}$, with $Hg_4Ag_{35}As_{10}Sb_1I_{25}S_{25}$ being preferred.

Any conventional compounding procedure known in the art may be used for the preparation of the vitreous sensor materials. In a preferred embodiment, the elemental components of relatively high purity are measured and ground together in an agate mortar under an inert gas such as argon. The mixture is then sealed in a silica tube evacuated to about 0.1 to 0.01 Pascal (Pa). The tube is heated slowly in a rocking furnace or the like to an upper range temperature of about 1100°–1300° Kelvin (K.). The melt should be allowed to mix and react for several hours ranging anywhere from 15–65 hours, then quenched to a solid amorphous glass or glassy/crystalline form and can be annealed to remove any strain.

The glass melts may then be cut into disks as is well known in the art and polished for use as the sensor element or membrane in an ion selective electrode, including convention ISE elements, as well as all solid state ISEs and ISFETs.

The following examples of the preparation of sensor materials and membranes made in accordance with the invention and the responses of selective electrodes using such membranes are for purposes of illustration only.

EXAMPLE I

SYNTHESIS OF CHALCOGENIDE GLASS SENSORS

A. Preparation of Cadmium Selective Composition

The elemental components listed in Table IA below were measured, thoroughly mixed and ground in an agate mortar under dry argon flow. The components were then sealed in an evacuated silica tube and heated to about 340°–380° K. and maintained at that temperature for a period ranging from 20–25 hours. The temperature was then increased over time to about 450°–500° K. and maintained for 15–20 hours, followed by additional heating to 800°–850° K. and held for 15–20 hours and to a final temperature of 1100°–1150° K. for 15–20 hours. The melt was then quenched at a mean quenching rate of 2° to 4° Kelvin per second (K./s) in the temperature range of 400°–500° K.

TABLE IA

| Cadmium Chalcogenide Glass Sensor | |
|---|---|
| Cd | 0.319 g |
| Ag | 2.601 g |
| As | 2.445 g |
| Sb | 0.518 g |
| I | 2.161 g |
| S | 1.956 g |

B, Preparation of Lead Selective Material

The elemental components listed below in Table IB were measured, thoroughly mixed and ground in an agate mortar under dry argon flow. The components were sealed in an evacuated silica tube and initially heated to a temperature ranging from 340°–380° K. and maintained at that temperature for about 30–35 hours. The temperature was then systematically increased to 450°–500° K. and held for 35–40 hours, to 800°–850° K. and maintained for 35–40 hours and finally to 1200°–1250° K. held for 35–40 hours. The melt was quenched at a mean quenching rate of 2° to 4° K./s in the temperature range of 400°–500° K.

TABLE IB

| Lead Chalcogenide Glass Sensor | |
|---|---|
| Pb | 3.036 g |
| Ag | 2.310 g |
| Ge | 1.064 g |
| I | 2.145 g |
| S | 1.445 g |

C. Preparation of Silver Selective Materials

The elemental components listed in Table IC below were mixed, ground in an agate mortar under dry argon flow and sealed in an evacuated silica tube. The tube was heated to 450°–500° K. and maintained at that temperature for about 10–15 hours. The temperature was then increased to 800°–850° K. and held for 15–20 hours, then to 1200°–1250° K. and maintained for 25–35 hours. The melt was quenched at a mean quenching rate of 2° to 4° K./s in the temperature range of 400°–500° K.

TABLE IC

| Silver Chalcogenide Glass Sensor | |
|---|---|
| Ag | 1.996 g |
| Ge | 3.134 g |
| Se | 4.870 g |

D. Preparation of Thallium Selective Materials

The elemental components listed below in Table ID were mixed, ground in an agate mortar under argon flow and sealed in an evacuated silica tube. The tube was heated slowly to about 450°–500° K. and maintained at that temperature for about 10–15 hours. After that the temperature was increased to 800°–850° K. and maintained for about 15–20 hours, followed by heating to 1200°–1250° K. for 25–30 hours. The melt was quenched at a mean quenching rate of 2° to 4° K./s in the temperature range of 400°–500°

K.

TABLE ID

| Thallium Chalcogenide Glass Sensor | |
| --- | --- |
| Tl | 5.056 g |
| Ge | 0.898 g |
| Se | 4.046 g |

E. Preparation of Mercury Selective Material

The elements listed below in Table IE were thoroughly mixed and ground in an agate mortar under dry argon flow. The components were then sealed in a silica tube and heated to an initial temperature ranging from 340°–380° K. for about 25–30 hours. The temperature was then increased to about 450°–500° K. and maintained for 20–25 hours, followed by heating to 800°–850° K. for 20–25 hours and to 1100°–1150° K. for 25–30 hours. The melt was quenched at a mean quenching rate of 2° to 4° K./s in the temperature range of 400°–500° K.

TABLE IE

| Mercury Chalcogenide Glass Sensor | |
| --- | --- |
| Hg | 0.851 g |
| Ag | 4.007 g |
| As | 0.795 g |
| Sb | 0.129 g |
| I | 3.367 g |
| S | 0.851 g |

All solid state ISEs were prepared from the above chalcogenide sensor materials. The material samples were cut from the melt as discs ranging in size from 5 to 10 millimeters (mm) in diameter and 1 to 3 mm thick. The discs were ground and polished for resistance measurement. Silver was evaporated on one side of the membrane and the edges were ground to remove any traces of silver which could short the sample. A metallic wire was attached to the silver coating using silver microadhesive.

The membrane was then sealed at the end of a plastic tube, with the silver coated surface being positioned on the interior of the tube and the metallic wire attached to a digital voltmeter. Electrochemical measurements were performed using chalcogenide glass sensor and silver/silver chloride reference electrode. Nitrate salts of corresponding metals were used for standard solution preparation. Nitric acid and potassium hydroxide were used to change pH of the standard solution. Selectivity coefficients were measured by mixed solution method.

EXAMPLE II

COMPARISON OF SENSOR MATERIALS OF THE PRESENT INVENTION WITH CONVENTIONAL CRYSTALLINE ELECTRODE MATERIALS AND PRIOR ART CHALCOGENIDE MATERIALS

A. Cadmium Chalcogenide Glass Sensor

The selectivity of the cadmium selective material prepared in Example IA above ($Cd_2Ag_{17}As_{23}Sb_3I_{12}S_{43}$) was compared with that of conventional polycrystalline electrode material comprising $CdS-Ag_2S$ and with prior art chalcogenide glass sensor compositions comprising $CdS-Ag_2S-As_2S_3$ and $CdI_2-Ag_2S-As_2S_3$.

TABLE II A

| Sensor Membrane Material | Selectivity Coefficients $\log K_{Cd^{2+}, Co^{2+}}$ |
| --- | --- |
| New Material $Cd_2Ag_{17}As_{23}Sb_3I_{12}S_{43}$ | $4(1) \times 10^{-5}$ |
| Prior Art Chalcogenides $CdS-Ag_2S-As_2S_3$ $CdI_2-Ag_2S-As_2S_3$. | $4(1) \times 10^{-4}$ |
| Conventional Crystalline $CdS-Ag_2S$ | $4(1) \times 10^{-4}$ |

It should be noted that the cadmium chalcogenide glass sensor of the present invention reveals better selectivity in the presence of alkali cations, cobalt and barium ions than conventional polycrystalline materials and prior art chalcogens. It is also 10 to 30 times less sensitive to the interference of nickel and thallium ions than conventional materials. Moreover, the acid stability of the inventive cadmium selective chalcogenide glass sensor is 30 to 100 times higher.

B. Lead Chalcogenide Glass Sensor

The selectivity of the lead selective material prepared in Example IB above ($Pb_{13}Ag_{19}Ge_{13}I_{15}S_{40}$) was compared with that of conventional polycrystalline electrode material comprising $PbS-Ag_2S$ and with prior art chalcogenide glass sensor compositions of $PbS-Ag2S-As2S3$ and $PbI_2-Ag_2S-As_2S_3$. The cadmium chalcogenide glass sensor of the present invention reveals better selectivity in the presence of cadmium and iron III) ions than conventional polycrystalline materials. This material is also 10 to 100 times less sensitive to strong oxidizing agents such as hydrogen peroxide or potassium permanganate.

The inventive lead selective material exhibits greater selectivity in the presence of hydrogen ions, wherein the working pH ranges of the compositions in 0.01M lead nitrate solution are as follows:

TABLE II B

| Sensor Membrane Material | Working pH Range |
| --- | --- |
| New Material $Pb_{13}Ag_{19}Ge_{13}I_{15}S_{40}$ | 1.3–6.5 |
| Prior Art Chalcogenides $PbS-Ag_2S-As_2S_3$ $PbI_2-Ag_2S-As_2S_3$ | 3.5–6.5 |
| Conventional Crystalline $PbS-Ag_2S$ | 2.0–6.5 |

C. Silver Chalcogenide Glass Sensor

The selectivity of the silver selective material prepared in Example IC above ($Ag_{15}Ge_{35}Se_{50}$) in accordance with the present invention was compared with that of conventional polycrystalline electrode material comprising $Ag_2S$ and with prior art chalcogenide glass sensor compositions of Ag-As-S and Ag-As-Se.

TABLE II C

| Sensor Membrane Material | Selectivity Coefficients $\log K_{Ag^+, Hg^{2+}}$ |
| --- | --- |
| New Material $Ag_{15}Ge_{35}Se_{50}$ | $3.0(9) \times 10^{-4}$ |
| Prior Art Chalcogenides Ag—As—S Ag—As—Se | $1.0(3) \times 10^{-3}$ |
| Conventional Crystalline $Ag_2S$ | $2.0(6) \times 10^{-2}$ |

In comparison with conventional silver ion-selective electrodes based on $Ag_2S$ polycrystalline mixture, this silver chalcogenide glass sensor is 10 to 100 times more stable in strong acid and corrosive media such as concentrated nitric acid and reveals better selectivity in the presence of $Hg^{2+}$ ions. The inventive material is 2 to 6 times more selective in the presence of mercury ions in comparison with prior chalcogenide glass sensors and 40 to 130 times more selective in comparison with conventional crystalline ion-selective electrodes.

D. Copper Chalcogenide Glass Sensor

The selectivity of a copper selective material $Cu_{10}Ag_{10}Ge_{32}Se_{48}$ prepared in accordance with the present invention was compared with that of conventional polycrystalline electrode materials such as $CuS-Ag_2S$, $Cu_2S-Ag_2S$, CuS and $Cu_2S$, and with prior art chalcogenide glass sensor compositions of Cu-Ag-As-Se.

TABLE II D

| Sensor Membrane Material | Selectivity Coefficients log $K_{Cu^{2+}, Ni^{2+}}$ |
|---|---|
| New Material $Cu_{10}Ag_{10}Ge_{32}Se_{48}$ | $4(1) \times 10^{-6}$ |
| Prior Art Chalcogenides Cu—Ag—As—Se | $3(1) \times 10^{-5}$ |
| Conventional Crystalline CuS—Ag2S, $Cu_2S$—$Ag_2S$, CuS and $Cu_2S$ | $3(1) \times 10^{-5}$ |

In comparison with conventional copper ion-selective electrodes based upon $CuS-Ag_2S$ or $Cu_2S-Ag_2S$ polycrystalline mixtures, the inventive copper chalcogenide glass sensor is 10 to 30 times less sensitive to the presence of interfering hydrogen ions. It is also an order of magnitude more selective in the presence of nickel ions in comparison with prior chalcogenide glass sensors and conventional crystalline electrodes.

E. Thallium Sensor Materials

The selectivity of the thallium selective material $Tl_{28}Ge_{14}Se_{58}$ prepared in accordance with the present invention was compared with that of conventional polycrystalline electrode materials. The present inventors are unaware of any prior art chalcogenide systems for the detection of thallium.

In comparison with polycrystalline thallium ion-selective electrodes based on $HgI_2$-TlI, AgI-TlI, or $Tl_2S$-$Tl_4Hg_6$ mixtures, thallium chalcogenide glass sensor is an order of magnitude more sensitive in diluted solutions of thallium ions, and its selectivity in the presence of alkali and hydrogen ions is 100 times higher.

F. Mercury Sensor Materials

The selectivity of the mercury selective material $Hg_4Ag_{35}As_{10}Sb_1I_{25}S_{25}$ prepared in accordance with the present invention was compared with that of conventional polycrystalline electrode materials. The present inventors are unaware of any prior art chalcogenide systems for the detection of thallium.

In comparison with polycrystalline mercury ion-selective electrodes based on AgI, $AgI-Ag_2S$, $HgI_2-HgS$ or $HgI_2-AgI-Ag_2S$ mixtures, mercury chalcogenide glass sensor reveals much more stable response in diluted solutions of mercury (II) ions without mechanical grinding or polishing and is an order of magnitude more sensitive in the presence of hydrogen ions.

While several embodiments of the invention, together with modifications thereof, have been described in detail herein it should be understood and will be evident that various further modifications are possible without departing from the scope of the invention.

We claim:

1. A method for detecting the concentration of a specific ion in solution, said method comprising measuring the concentration of said ion in solution by contacting the solution with a sensing element that is selective for said specific ion, said sensing element comprising a vitreous chalcogenide membrane characterized by a modified surface layer of thickness generally ranging from about 20 to 200 nm when place in contact with said solution, said modified surface layer exhibiting an ionic conductivity ranging from $10^{-7}$ to $10^{-2}$ S/cm, a diffusion coefficient ranging from $10^{-11}$ to $10^{-6}$ cm$^2$/s and having a ratio electronic to ionic conductivity no greater than 1.0.

2. A method according to claim 1 wherein said sensing element for detecting cadmium ions comprises 1 to 7% by weight cadmium, 8 to 30% by weight silver, 15 to 30% by weight arsenic, 6 to 18% iodide, 2 to 10% antimony and 5–68% sulfur.

3. A method according to claim 1, wherein said sensing element for detecting lead ions comprises 3 to 15% by weight lead, 10 to 30% by weight silver, 10 to 25% by weight germanium, 5 to 20% iodide and 10–72% sulfur.

4. A method according to claim 1, wherein said sensing element for detecting silver ions comprises 6 to 30% by weight silver, 25 to 40% by weight geranium and 30–69% selenium.

5. A method according to claim 1, wherein said sensing element for detecting thallium ions comprises 20 to 35% by weight thallium, 14 to 40% by weight germanium and 25–64% selenium.

6. A method according to claim 1, wherein said sensing element for detecting copper ions comprises 5 to 20% by weight copper, 5 to 20% by weight silver, 18 to 32% by weight germanium and 28–72% selenium.

7. A method according to claim 1, wherein said sensing element for detecting mercury ions comprises 2 to 10% by weight mercury, 25 to 40% by weight silver, 7 to 16% by weight arsenic, 1 to 5% by weight antimony, 20 to 30% of iodide and 1–45% sulfur.

8. In an analytical device for potentiometric determination of the concentration of ions in solution, an element sensitive to selected ions is provided comprising a vitreous chalcogenide membrane characterized by a modified surface layer of a thickness generally ranging from about 20 to 200 nm when placed in contact with said solution, said modified surface layer exhibiting an ionic conductivity ranging from $10^{-7}$ to $10_{-2}$ S/cm, a diffusion coefficient ranging from ($10^{-11}$ to $10^{-6}$ cm$^2$/s) and having a ratio of electronic to ionic conductivity no greater than 1.0.

\* \* \* \* \*